United States Patent
Den Heeten et al.

(10) Patent No.: US 9,353,039 B2
(45) Date of Patent: May 31, 2016

(54) PROCESS FOR THE PRODUCTION OF POLYETHER POLYOLS

(71) Applicant: Huntsman International LLC, The Woodlands, TX (US)

(72) Inventors: Rene Den Heeten, Den Haag (NL); Paul Anton Termorshuizen, Rockanje (NL)

(73) Assignee: HUNTSMAN INTERNATIONAL LLC, The Woodlands, TX (US)

(*) Notice: Subject to any disclaimer, the term of this patent is extended or adjusted under 35 U.S.C. 154(b) by 0 days.

(21) Appl. No.: 14/402,126

(22) PCT Filed: Apr. 25, 2013

(86) PCT No.: PCT/EP2013/058599
§ 371 (c)(1),
(2) Date: Nov. 19, 2014

(87) PCT Pub. No.: WO2013/178410
PCT Pub. Date: Dec. 5, 2013

(65) Prior Publication Data
US 2015/0133696 A1    May 14, 2015

(30) Foreign Application Priority Data
May 29, 2012 (EP) ..................................... 12169832

(51) Int. Cl.
C07C 41/44 (2006.01)
C07C 41/34 (2006.01)
C08G 65/30 (2006.01)

(52) U.S. Cl.
CPC ................. *C07C 41/44* (2013.01); *C07C 41/34* (2013.01); *C08G 65/30* (2013.01)

(58) Field of Classification Search
CPC ......... C07C 41/04; C07C 41/34; C08G 65/30
See application file for complete search history.

(56) References Cited

U.S. PATENT DOCUMENTS

| | | | |
|---|---|---|---|
| 3,582,491 A | 6/1971 | Louvar et al. | |
| 3,715,402 A | 2/1973 | Louvar et al. | |
| 3,823,145 A | 7/1974 | Louvar et al. | |
| 3,833,669 A | 9/1974 | Gehm et al. | |
| 4,254,287 A | 3/1981 | Ziegenhain et al. | |
| 4,306,943 A | 12/1981 | Mori et al. | |
| 4,482,750 A | 11/1984 | Hetzel et al. | |
| 4,507,475 A | 3/1985 | Straehle et al. | |
| 4,985,551 A | 1/1991 | Perry et al. | |
| 9,012,695 B2 * | 4/2015 | De Mars et al. | 568/621 |
| 9,040,753 B2 * | 5/2015 | Chen | 568/617 |
| 2013/0338331 A1 * | 12/2013 | Lorenz et al. | 528/76 |

FOREIGN PATENT DOCUMENTS

| | | |
|---|---|---|
| EP | 0 982 341 | 8/1999 |
| WO | 01/88015 | 11/2001 |
| WO | 04/000914 | 12/2003 |
| WO | 2010/145899 | 12/2010 |

* cited by examiner

*Primary Examiner* — Shailendra Kumar
(74) *Attorney, Agent, or Firm* — Robert A. Diaz

(57) ABSTRACT

A method to provide polyether polyols comprises the steps of •providing a crude polyether polyol mixture comprising polyether polyol and a base catalyst; •neutralizing said base catalyst; •removing, in a first dehydration step, at least part of the water from the neutralized polyether polyol; •redissolving at least part of the salt crystals obtained by removal of at least part of the water; •removing, in a second dehydration step, at least part of the water from the neutralized polyether polyol mixture, thereby providing salt crystals; •removing the salt crystals from the neutralized polyether polyol, thereby providing the polyether polyol mixture.

9 Claims, No Drawings

PROCESS FOR THE PRODUCTION OF POLYETHER POLYOLS

This application is the National Phase of International Application PCT/EP2013/058599 filed Apr. 25, 2013 which designated the U.S. and which claims priority to Foreign Application No. 12169832.8 filed May 29, 2012. The noted applications are incorporated herein by reference.

The present invention relates to the production of polyether polyols, and more in particular to the neutralization and removal of the base catalyst used in the production of polyether polyols.

Methods for preparing polyether polyols, also sometimes referred to as poly (alkylene oxide)polyols, typically involve reacting a starting compound having a plurality of active hydrogen atoms with one or more alkylene oxides in the presence of a base catalyst, preferably a strong base such as potassium hydroxide. Suitable starting compounds are a.o. polyfunctional alcohols, typically comprising 2 to 6 hydroxyl groups. Examples of such alcohols are glycol, e.g. diethylene glycol, dipropylene glycol, glycerol, di- and polyglycerols, pentaerythritol, trimethylolpropane, diethanolamine, triethanolamine, sorbitol, mannitol, etc. Alkylene oxides used are typically ethylene oxide, propylene oxide, butylene oxide or mixtures of two or more of these.

After the addition of the alkylene oxides to the starting material, a crude, basic polyether polyol is obtained, which needs neutralization of the base catalyst.

After neutralization, several steps are required to provide a polyether polyol meeting the specifications for further use of the polyether polyol. The polyether polyol may e.g. be used as a raw material in polyurethane production, where the polyol is, in general, reacted with a polyisocyanate component, such as methylene diphenyl diisocyanate (MDI) or toluene diisocyanate (TDI).

U.S. Pat. No. 4,306,943 describes a process for the preparation of polyether polyols in which the polyols are neutralized by adding to the crude polyether polyol a mineral acid having a dissociation constant greater than $10^{-3}$ at 25° C. and from 0.01 to 0.3% wt, based on the weight of crude polyol, of the hydrate of a metal salt of the applied mineral acid for promoting the crystal growth of salt formed from the alkaline catalyst by the neutralization. The water is subsequently removed by distillation and the reaction mixture is filtered. A drawback of this method is that the metal salt hydrates must be prepared in a separate process step and that the amount of filtration residue is increased by this addition.

The disadvantage of this and other processes of prior art is that the neutralization which causes crystallization of salt, provides small crystals and/or crystals which have a considerable variation in particle size. This causes the removal of the particles, e.g. by filtration, to become difficult.

The present invention aims to provide a process for the preparation of polyether polyols, wherein the neutralization of the reaction medium and removal of the base catalyst (also referred to as alkaline catalyst or alkaline polymerization catalyst), catalyzing the reaction between the alkene oxide (epoxide) and the starting polyol or the alcohol groups of the polyether polyol, is optimized with regard to particle size, particle size distribution and/or process time.

According to the present invention, a method to provide polyether polyols is provided. The method comprises the steps of
  providing a crude polyether polyol mixture comprising polyether polyol and a base catalyst;
  mixing the crude polyether polyol mixture with an acid and water, thereby neutralizing said base catalyst and providing a first neutralized polyether polyol mixture;
  removing, in a first dehydration step, at least part of the water from said first neutralized polyether polyol, thereby providing a first dehydrated neutralized polyether polyol mixture having a water content of 0.00 to 5.00% w and comprising said polyether polyol and salt of said base catalyst and said acid, said salt being present as salt crystals;
  redissolving at least part of the salt by adding water to said first dehydrated neutralized polyether polyol mixture, thereby providing a second neutralized polyether polyol mixture;
  removing, in a second dehydration step, at least part of the water from said second neutralized polyether polyol mixture, thereby providing a second dehydrated neutralized polyether polyol mixture comprising said polyether polyol and salt of said base catalyst and said acid, said salt being present as salt crystals;
  removing said salt crystals from said second dehydrated neutralized polyether polyol, thereby providing the polyether polyol mixture.

According to some embodiments of the present invention, the polyether polyol mixture may comprise 0.00 to 0.08 w % water, said w % being expressed over the total weight of the polyether polyol mixture.

In the step of mixing the crude polyether polyol mixture with an acid and water, thereby neutralizing the base catalyst and providing the first neutralized polyether polyol mixture, the water and the acid may be added separately, or the acid and water may be added as an aqueous acid solution. Optionally only part of the added water is used to make the aqueous acid solution, whereas the remaining water is added as such.

Hence according to some embodiments of the present invention, the acid may be added to the crude polyether polyol as an aqueous acid solution.

The base catalyst used to catalyze the reaction between the alkylene oxides and the alcohol groups during the polymerization of the polyether polyol, is typically a strong base such as an alkali metal hydroxide, e.g. sodium hydroxide, potassium hydroxide or cesium hydroxide, or mixtures thereof, whereas most preferably potassium hydroxide is used. Typically an amount in the range of 0.05 to 2 w %, e.g. in the range of 0.10 to 0.35 w %, and most preferred an amount in the range of 0.13 to 0.29 w % of catalyst, said w % based on the total weight of the polyether polyol to be prepared in the crude polyether polyol mixture is used in the reaction mixture during the polymerization reaction.

Hence according to some embodiments of the present invention, the base catalyst is potassium hydroxide, sodium hydroxide, cesium hydroxide or combinations thereof.

The crude polyether polyol mixture is provided by catalytically polymerizing a starting compound with alkylene oxides (also referred to as epoxides). Suitable starting compounds are a.o. polyfunctional alcohols, typically comprising 2 to 6 hydroxyl groups. Examples of such alcohols are glycols, e.g. diethylene glycol, dipropylene glycol, glycerol, di- and polyglycerols, pentaerythritol, trimethylolpropane, diethanolamine, triethanolamine, sorbitol, mannitol, ethylene glycol, 1,2-propylene glycol, sucrose, 1,2,6-hexanetriol, or polyamines such as ethylene diamine and diaminodiphenylmethane (MDA), and any combination thereof.

The alkylene oxides used are typically ethylene oxide (EO), propylene oxide (PO), butylene oxide (BO) or mixtures of two or more of these.

The polyether polyol comprising more than one type of alkylene oxide may be a so-called block polyether comprising at least two different alkylene oxides, obtained e.g. by reacting the starting compound with one of the alkylene oxide components. After termination of this polyaddition reaction, the intermediate polyether polyol is reacted with an other of the alkylene oxides. This sequential addition of blocks of alkylene oxides can be repeated. As such blocks of different alkylene oxides are added to the polyether polyol.

The polyether polyol comprising more than one type of alkylene oxide may be a so-called random polyether comprising at least two different alkylene oxides, obtained e.g. by reacting the starting compound with a combination of at least two different alkylene oxide components. After termination of this polyaddition reaction, the different alkylene oxides will be at random in the sequences of the polyether chains.

It is understood that also a combination of blocks of only one alkylene oxide, and blocks of at random placed alkylene oxides may be provided to the polyether polyols.

Though polyols with an EO content up to 100% can be used, most preferably, the polyether polyol comprises less than 80% EO, an EO content of 5 to 80% EO, and most preferred an EO content in the range of 5 to 35% such as in the range of 10 to 30%. The EO content is the number of EO-monomers in the polyol over the total of alkyloxide monomers in the polyol, expressed as a percentage.

These EO may be present at random or as blocks, and are preferably combined with PO in the polyether polyol. Most preferably the polyether polyol is a combined EO-PO polyether polyol, meaning that the polyether polyol is provided by reacting the starting component with alkylene oxides selected from EO and PO only, and this at random or in sequences to provide block polymers.

The polyether polyols may be EO tipped, which means that at least the last alkylene oxide added to the polyol is an EO.

Hence according to some embodiments of the present invention, the EO content of the polyether polyol may be in the range of 5 to 80%.

The crude, alkaline, polyether polyol mixture is mixed with an acid, optionally provided as an aqueous acid solution. The base catalyst is thereby neutralized. To neutralize the crude polyether polyol, a mono- or polyprotic acid is added to the unneutralised polyether polyol, such that "A" moles of the mono- or polyprotic acid are added to the unneutralised polyether polyol, such that $B \leq n*A$, wherein B are the moles of protons necessary to completely neutralize the crude polyether polyol and n being the number of protons which said mono- or polyprotic acid can donate.

As the base catalyst is typically an alkali metal hydroxide, B typically is the number of moles of alkali metal hydroxide in the crude polyether polyol. When a monoprotic acid such as hydrogen chloride (HCl) is used, typically 1.00 to 1.064 moles of monoprotic acid per mole of alkali metal hydroxide is added. For diprotic acids, such as adipic acid, typically 0.50 to 0.53 mole of acid per mole of alkali metal hydroxide is added.

The acidity of the neutralized polyether polyol, i.e. the acid value, is expressed as the weight of KOH (mg) per gram of polyether that needs to be added to neutralize the acid. Typically the neutralized polyether polyol has an acid value of 0.01 to 0.1 mgKOH/g.

The acid used to neutralize the base catalyst is added as such in combination with water that is added, or as an aqueous solution. This water may be added all as part of the aqueous acid solution, or alternatively, only a part of this water is used to provide the acid aqueous solution, the remaining water is added separately.

Typically 0.5 to 10 parts by weight of water is added per 100 parts by weight of the polyether polyol in the crude polyether polyol.

Suitable acids are a.o. anorganic acids such as $H_2SO_4$, $H_3PO_4$, HCl, $CO_2$ (added as gas forming $H_2CO_3$ in water) or organic acids such as formic acid, tartaric acid, adipic acid, oxalic acid, malonic acid, succinic acid, glutaric acid, maleic acid, fumaric acid, acetic acid, citric acid, pimelic acid, suberic acid, azelaic acid and sebacic acid, or any mixture of these acids.

According to some embodiments of the present invention, an aqueous acid solution of the acid may be used to neutralize the crude polyether polyol mixture.

Typically, when KOH or NaOH is used as base catalyst, and adipic acid is used to neutralize the crude polyether polyol, 0.49 to 0.56 moles of adipic acid, and preferably 0.5 to 0.53 moles of adipic acid are added for each mole of KOH or NaOH.

The crude, alkaline, polyether polyol mixture is preferably brought or kept at a temperature of 25 to 150 deg C., e.g. at a temperature in the range of 70 to 150 deg C., more preferred at a temperature of 80 deg C. to 130 deg C. before, during and/or after neutralization.

After neutralization of the crude, alkaline, polyether polyol mixture, at least a part of the water present in this mixture is removed thereby providing a first dehydrated neutralized polyether polyol mixture comprising the polyether polyol and the salt formed by the base catalyst and the added acid. Because of the removal of at least part of the water, some or all the salt is crystallized and hence provides salt crystals.

This first dehydration process may be a distillation process, i.e. by heating the crude neutralized polyether polyol mixture to remove the water and/or subjecting the crude neutralized polyether polyol mixture to a vacuum for removing at least part of the water.

Most preferred, the temperature of the crude neutralized polyether polyol mixture is brought or kept in the range of 25 to 250 deg C., such as in the range of 70 to 160 deg C., and more preferred in the range of 80 deg C. to 140 deg C., while the pressure of the reactor is brought to a pressure of 0.20 to 0.01 bara.

The term "bara" means "bar absolute", i.e. the pressure expressed in the unit bar, zero-referenced against a perfect, i.e. absolute, vacuum. One bar equals 100000 Pa.

The water in the first dehydrated neutralized polyether polyol mixture after removal of at least part of the water is in the range of 0.00 to 5.00% w, more preferably in the range of 0.01 to 3.00% w, and more preferred in the range of 0.10 to 1.00% w.

Optionally, though not necessarily, a part of the formed crystals may be removed, e.g. filtered, from the first dehydrated polyether polyol mixture.

After dehydration in the first dehydration step, water is added again to the first dehydrated neutralized polyether polyol.

This water may be e.g. distilled water (or condensate) or demineralised water.

The addition of the water causes at least part, and preferably all the salt crystals to redissolve.

Most preferred, the temperature of the dehydrated neutralized polyether polyol mixture is brought or kept in the range of 25 to 250 deg C., such as in the range of 25 to 150 deg C., more preferred in the range of 80 deg C. to 140 deg C. The temperature of the water added can be used to control the temperature of the dehydrated neutralized polyether polyol mixture during this redissolving step. The water added is also brought or kept in the range of 25 to 250 deg C., typically in the range of 60 to 100 deg C., and more preferred in the range 85 to 95 deg C.

The amount of water added may be in the range of 0.5 to 10 parts by weight, and more preferred in the range of 1 to 5 parts by weight of water per 100 parts by weight of the polyether polyol in the crude polyether polyol.

Hence according to some embodiments of the present invention, the amount of water added to the first dehydrated neutralized polyether polyol mixture may be in the range of 0.5 to 10 parts by weight per 100 parts by weight of the polyether polyol in the crude polyether polyol.

Optionally but not preferred, during or after the addition of the water, further components such as crystal growth promoting components (also referred to as seeds) may be added, e.g. the hydrate of a metal salt of the applied mineral acid.

After redissolving at least part of the salt crystals by adding water to the first dehydrated neutralized polyether polyol mixture, at least a part of the water present in the second crude neutralized polyether polyol mixture is removed thereby providing a second dehydrated neutralized polyether polyol mixture comprising the polyether polyol and salt formed by the base catalyst and the added acid. Because of the removal of at least part of the water, some or all the salt is again crystallized and hence provides salt crystals.

Though it is not understood why, the salt crystals obtained after redissolving and recrystallisation have a larger crystal size and/or a more narrow size distribution, which allows a better and more efficient control and removal of the salt crystal in the next step. In particular in case a filtration process is used to remove the salt crystals from the mixture, the improved crystal size uniformity and crystal size increase allows a more efficient and better controllable filtration process.

Typical dimensions of the salt crystals are from less than 10 micron to about 150 micron or even more. Using the method according to the present invention, a significant amount of crystals have a dimension of 10 micron or more, whereas the presently known processes often provide the majority of the crystals to have a dimension of less than 10 microns.

This second dehydration process may be a distillation process, i.e. by heating the second crude neutralized polyether polyol mixture to remove the water and/or subjecting the second crude neutralized polyether polyol mixture to a vacuum for removing at least part of the water.

Most preferred, the temperature of the crude neutralized polyether polyol mixture is brought or kept in the range of 25 to 250 deg C., such as in the range of 70 to 160 deg C., and more preferred in the range of 80 deg C. to 140 deg C., while the pressure of the reactor is brought to a pressure of 0.20 to 0.01 bara. Optionally the temperature may be gradually raised to about 110 to 150 deg C. before ending this dehydration step.

The water in the second dehydrated neutralized polyether polyol mixture after removal of at least part of the water is less than 0.08 w %, more preferably in the range of 0.01 w % to max 0.08 w %.

After dehydration of the second crude neutralized polyether polyol mixture, the salt crystals are removed from the second dehydrated neutralized polyether polyol. As such a polyether polyol mixture comprising said polyether polyol and optionally water, up to 0.08 w % may be provided, said w % being expressed over the total weight of the polyether polyol mixture.

The removal of the salt crystals is preferably a filtration step where the second dehydrated neutralized polyether polyol is to flow through a filter, which retains the salt crystals on the filter and let the polyol and water, if still present, pass through the filter.

Hence according to some embodiments of the present invention, removal of the salt crystals may be obtained by filtration.

The polyether polyol may e.g. be used as a raw material in polyurethane production, where the polyol is, in general, reacted with a polyisocyanate component, such as methylene diphenyl diisocyanate (MDI) or toluene diisocyanate (TDI).

The independent and dependent claims set out particular and preferred features of the invention. Features from the dependent claims may be combined with features of the independent or other dependent claims as appropriate.

The above and other characteristics, features and advantages of the present invention will become apparent from the following detailed description, which illustrate, by way of example, the principles of the invention. This description is given for the sake of example only, without limiting the scope of the invention.

The present invention will be described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art.

4 polyols are prepared according the present invention.

Polyol # I is a glycerol-started EO-tipped EO/PO polyether polyol with average molecular weight of 6000. The polyol comprises 15.2 w % of EO (on total of EO and PO).

Polyol # II is a glycerol-started EO-tipped EO/PO polyether polyol with average molecular weight of 6000. The polyol comprises 27.4 w % of EO (on total of EO and PO).

Polyol # III is a dipropylene glycol-started EO-tipped EO/PO polyether polyol with average molecular weight of 3700. The polyol comprises 16.0 w % of EO (on total of EO and PO).

Polyol # IV is a glycerol-started EO-tipped EO/PO polyether polyol with average molecular weight of 5000. The polyol comprises 17.0 w % of EO (on total of EO and PO). The term "EO/PO polyether polyol" above refers to a polyol comprising both EO monomers and PO monomers in its polymer chain.

The above four polyols are made using a method according to the invention. The results are set out in table I under (polyol suffix "a"). For comparison, the same polyols are made, however with no addition of water after the first dehydration step, and no second dehydrating step. The results are set out in table II under (polyol suffix "b").

EXAMPLES ACCORDING TO THE INVENTION

Some example of a method according to the invention is carried out by the following general procedure. A crude alkaline polyether polyol mixture is provided, comprising a polyether polyol and KOH as alkali (base) catalyst.

The crude alkaline polyether polyol mixture, contained in a vessel (hereinafter neutralization vessel), is neutralized by the addition of an aqueous adipic acid solution at 95 deg C. The aqueous adipic acid solution contains about 0.51 moles of adipic acid per mole of base catalyst and 2.5 parts by weight of water (condensate) per 100 parts by weight of the polyol in the crude polyether polyol mixture. As such a first neutralized polyether polyol mixture is provided. After 15 to 30 minutes of neutralization, the water is removed by gradually decreasing the pressure in the vessel from 1.8 bara to 0.1 bara over a time span of 2 hours while maintaining the temperature at 95 deg C. As such a first dehydrated neutralized polyether polyol mixture is provided.

When the pressure in the neutralization vessel reaches 0.1 bara, the vessel is vented to atmospheric pressure. Next, 5 parts by weight of water (condensate) per 100 parts by weight of the polyol in the crude polyether polyol mixture are added. Typically the temperature of the water is between about 80 and 100° C. As such a second crude neutralized polyether polyol mixture is provided. The dispersed potassium adipate is allowed to redissolve for 15 minutes at 95 deg C.

Next, the water is removed a second time by gradually reducing the pressure from 1.8 bara to 0.25 bara, gradually increasing the temperature of the polyol mixture to 105 or 115 deg C., over a varying time span (see tables). Thereafter, the pressure is further gradually reduced to less than 0.01 bara over a varying time span (see tables), meanwhile gradually increasing the temperature of the polyol mixture to 140 deg C.

While water is progressively removed, potassium adipate crystals are formed. When water content is within specification, i.e. at maximum 0.08 w % water, the vessel is vented to atmospheric pressure.

As such a second dehydrated neutralized polyether polyol is provided.

A filtration process is carried out to this heated second dehydrated neutralized polyether polyol. The potassium adipate salts that are formed precipitate as coarse crystals, so that filtration presents no problems, even without a filtration aid. The polyether polyol mixtures thus obtained have residual alkali contents of less than 5 ppm and water contents of max 0.08%. The acidity of these samples was determined obtaining values varying between 0.01-0.10 mgKOH/g.

FOLLOWING EMBODIMENTS OF THE PRESENT INVENTION WERE REALIZED

TABLE I

| | Polyol | | | |
|---|---|---|---|---|
| | # Ia | # IIa | # IIIa | # IVa |
| KOH/batch[1] | 0.18 w % | 0.18 w % | 0.18 w % | 0.18 w % |
| Mol Adipic Acid/mol KOH | 0.52 | 0.51 | 0.51 | 0.51 |
| Amount water #1[1] | 2.5% | 2.5% | 2.5% | 2.5% |
| T neutralization | 95 C. | 95 C. | 95 C. | 95 C. |
| DH profile #1 | 1.8 > 0.1 bara T = 95 C., t = 2 h | 1.8 > 0.1 bara T = 95 C., t = 2 h | 1.8 > 0.1 bara T = 95 C., t = 2 h | 1.8 > 0.1 bara T = 95 C., t = 2 h |
| Amount water #2[1] | 5% | 5% | 5% | 5% |
| DH profile #2 | 1) 1.8 > 0.25 bara, T = 125 C., t = 2.25 h 2) 0.25 > minimum bara, T = 140 C., t = 1.75 h | 1) 1.8 > 0.25 bara, T = 105 C., t = 3.25 h 2) 0.25 > minimum bara, T = 140 C., t = 2.25 h | 1) 1.8 > 0.25 bara, T = 105 C., t = 3 h 2) 0.25 > minimum bara, T = 140 C., t = 2 h | 1) 1.8 > 0.25 bara, T = 105 C., t = 3.25 h 2) 0.25 > minimum bara, T = 140 C., t = 2 h |
| Filter specs[2] | C | B | A | B |

[1]weight percentage over weight of polyol in the crude polyol mixture
[2]Filtration specs: Time required for the filtration of 40 ton polyol:
A <90 min: very fast filtration
B 90 < x < 120 min: fast filtration
C 120 < x < 240 min: medium filtration
[D] >240 min: slow filtration

COMPARATIVE EXAMPLES

The same polyols are treated in a similar way as set out above, however with no addition of water after the first dehydration step, and no second dehydrating step. The temperature and the pressure were gradually changed as set out in table II. Also here, the minimum pressure is less than 0.01 bara. The salt crystals after the first dehydration step are filtered out in an identical way to provide the polyether polyol mixture according to prior art.

TABLE II

| | Polyol | | | |
|---|---|---|---|---|
| | # Ib | # IIb | # IIIb | # IVb |
| KOH/batch[1] | 0.18 w % | 0.18 w % | 0.18 w % | 0.18 w % |
| Mol Acid/mol KOH | 0.52 | 0.51 | 0.51 | 0.51 |
| Amount water #1[1] | 2.5% | 2.5% | 2.5% | 2.5% |
| T neutralization | 95 C. | 95 C. | 95 C. | 95 C. |
| DH profile #1 | 1.9 > minimum bara T = 95 > 140 C., t = 3 h | 1.9 > minimum bara T = 95 > 140 C., t = 3 h | 1.9 > minimum bara T = 95 > 140 C., t = 3 h | 1.9 > minimum bara T = 95 > 140 C., t = 3 h |
| Filter specs[2] | D | D | C | C |

[1] weight percentage over weight of polyol in the crude polyol mixture
[2] Filtration specs: Time required for the filtration of 40 ton polyol:
[A] <90 min: very fast filtration
[B] 90 < x < 120 min: fast filtration
C 120 < x < 240 min: medium filtration
D >240 min: slow filtration Water content was determined following ASTM D4672, potassium content according to ASTM D4668 and acidity following ASTM D4662.

PSD Measurements

From the polyols Ia and Ib, the particle size distribution (PSD) of the crystals after the last filtration step was measured. The results are set out in table III.

TABLE III

| PSD (vol %) | Polyol Ia | Polyol Ib |
|---|---|---|
| <10 micron | 14 | 63 |
| 10-20 micron | 22 | 27 |
| 20-50 micron | 44 | 9 |
| 50-100 micron | 18 | 1 |
| >100 micron | 2 | 0 |

As one may notice, using standard practice 63% vol of the crystals have a dimension of less than 10 microns. The method according to the invention provide only 14% vol of the crystals to have such small dimension, whereas the majority of the particles have a dimension in the range of 10 to 100 microns.

It is to be understood that although preferred embodiments and/or materials have been discussed for providing embodiments according to the present invention, various modifications or changes may be made without departing from the scope and spirit of this invention.

The invention claimed is:

1. A method to provide polyether polyols, the method comprising the steps of
   providing a crude polyether polyol mixture comprising polyether polyol and a base catalyst;
   mixing the crude polyether polyol mixture with an acid and water, thereby neutralizing said base catalyst and providing a first neutralized polyether polyol mixture;
   removing, in a first dehydration step, at least part of the water from said first neutralized polyether polyol, thereby providing a first dehydrated neutralized polyether polyol mixture having a water content in the range 0.00 to 5.00% w and comprising said polyether polyol and salt of said base catalyst and said acid, said salt being present as salt crystals;
   redissolving at least part of the salt by adding water to said first dehydrated neutralized polyether polyol mixture, thereby providing a second neutralized polyether polyol mixture;
   removing, in a second dehydration step, at least part of the water from said second neutralized polyether polyol mixture, thereby providing a second dehydrated neutralized polyether polyol mixture comprising said polyether polyol and salt of said base catalyst and said acid, said salt being present as salt crystals;
   removing said salt crystals from said second dehydrated neutralized polyether polyol, thereby providing the polyether polyol mixture.

2. The method according to claim 1, wherein the polyether polyol mixture comprises 0.00 to 0.08 w % water, said w % being expressed over the total weight of the polyether polyol mixture.

3. The method according to claim 1, wherein the acid is added to the crude polyether polyol as an aqueous acid solution.

4. The method according to claim 1, wherein the base catalyst is potassium hydroxide, sodium hydroxide, cesium hydroxide or combinations thereof.

5. The method according to claim 1, wherein the ethylene oxide content of the polyether polyol is in the range of 5 to 80%.

6. The method according to claim 1, wherein the water content of the first dehydrated neutralized polyether polyol mixture is in the range of 0.01 to 3.00% w.

7. The method according to claim 6, wherein the water content of the first dehydrated neutralized polyether polyol mixture is in the range of 0.10 to 1.00% w.

8. The method according to claim 1, wherein the amount of water added to the first dehydrated neutralized polyether polyol mixture is in the range of 0.5 to 10 parts by weight per 100 parts by weight of the polyether polyol in the crude polyether polyol.

9. The method according to claim 1, wherein removal of the salt crystals is obtained by filtration.

* * * * *